(12) United States Patent
Donati

(10) Patent No.: US 8,293,980 B2
(45) Date of Patent: Oct. 23, 2012

(54) LETTUCE VARIETIES AND METHOD OF PRODUCTION

(75) Inventor: Franco Donati, Fidenza (IT)

(73) Assignee: ISI Sementi S.p.A., Fidenza (PR) (IT)

( * ) Notice: Subject to any disclaimer, the term of this patent is extended or adjusted under 35 U.S.C. 154(b) by 268 days.

(21) Appl. No.: 12/767,738

(22) Filed: Apr. 26, 2010

(65) Prior Publication Data

US 2011/0265200 A1  Oct. 27, 2011

(51) Int. Cl.
*A01H 1/00* (2006.01)
*A01H 5/00* (2006.01)
*A01H 5/10* (2006.01)

(52) U.S. Cl. ......... 800/305; 435/410; 800/260; 800/298

(58) Field of Classification Search ....................... None
See application file for complete search history.

(56) References Cited

U.S. PATENT DOCUMENTS

| | | | |
|---|---|---|---|
| 7,126,045 B2 | 10/2006 | Knerr | |
| 7,332,653 B2 * | 2/2008 | Knerr | ........................... 800/305 |
| 7,371,931 B1 | 5/2008 | Knerr | |
| 7,632,986 B1 | 12/2009 | Maggioni | |
| 7,696,413 B2 | 4/2010 | Maggioni | |

* cited by examiner

*Primary Examiner* — Eileen B O Hara
(74) *Attorney, Agent, or Firm* — Morrison & Foerster LLP

(57) ABSTRACT

Lettuce varieties ISI 43630 and ISI 43637 are described. Both ISI 43630 and ISI 43637 are red leaf lettuce varieties.

30 Claims, No Drawings

LETTUCE VARIETIES AND METHOD OF PRODUCTION

I. FIELD OF THE INVENTION

The present invention is directed to new varieties of lettuce, *Lactuca sativa*.

II. BACKGROUND OF THE INVENTION

Lettuce is an important crop consumed worldwide. There is a need to develop new varieties which display improved characteristics.

III. SUMMARY OF THE INVENTION

In order to meet these needs, the present invention is directed to improved lettuce varieties. In one embodiment, the present invention is directed to lettuce, *Lactuca sativa*, seed designated as ISI 43630 having ATCC Accession Number PTA-10859. In one embodiment, the present invention is directed to a *Lactuca sativa* lettuce plant and parts isolated therefrom produced by growing ISI 43630 lettuce seed. In another embodiment, the present invention is directed to a *Lactuca sativa* plant and parts isolated therefrom having all the physiological and morphological characteristics of a *Lactuca sativa* plant produced by growing ISI 43630 lettuce seed having ATCC Accession Number PTA-10859In still another embodiment, the present invention is directed to an $F_1$ hybrid *Lactuca sativa* lettuce seed, plants grown from the seed, and a head isolated therefrom having ISI 43630 as a parent, wherein ISI 43630 is grown from ISI 43630 lettuce seed having ATCC Accession Number PTA-10859

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from ISI 43630 lettuce plants. In another embodiment, the present invention is further directed to tissue culture of ISI 43630 lettuce plants.

In still another embodiment, the present invention is further directed to packaging material containing ISI 43630 plant parts. Such packaging material includes but is not limited to boxes, plastic bags, etc. The ISI 43630 plant parts may be combined with other plant parts of other plant varieties.

In yet another embodiment, the present invention is further directed to a method of selecting lettuce plants comprising a) growing ISI 43630 lettuce plants wherein the ISI 43630 plants are grown from lettuce seed having ATCC Accession Number PTA-10859 and b) selecting a plant from step a). In another embodiment, the present invention is further directed to lettuce plants, plant parts and seeds produced by the lettuce plants wherein the lettuce plants are isolated by the selection method of the invention.

In another embodiment, the present invention is further directed to a method of breeding lettuce plants comprising crossing a lettuce plant with a plant grown from ISI 43630 lettuce seed having ATCC Accession Number PTA-10859.In still another embodiment, the present invention is further directed to lettuce plants, lettuce parts from the lettuce plants, and seeds produced therefrom where the lettuce plant is isolated by the breeding method of the invention.

The present invention is further directed to *Lactuca sativa* lettuce seed designated asISI 43637 having ATCC Accession Number PTA-10858. In one embodiment, the present invention is directed to a *Lactuca sativa* lettuce plant and parts isolated therefrom produced by growing ISI 43637 lettuce seed. In another embodiment, the present invention is further directed to a *Lactuca sativa* plant and parts isolated therefrom having all the physiological and morphological characteristics of a *Lactuca sativa* plant produced by growing ISI 43637 lettuce seed having ATCC Accession Number PTA-10858.In still another embodiment, the present invention is further directed to an $F_1$ hybrid *Lactuca sativa* lettuce seed, plants grown from the seed and a head isolated therefrom having ISI 43637 as a parent wherein ISI 43637 is grown from ISI 43637 lettuce seed having ATCC Accession Number PTA-10858.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from ISI 43637 lettuce plants. In yet another embodiment, the present invention is further directed to tissue culture of ISI 43637 lettuce plants.

In still another embodiment, the present invention is further directed to packaging material containing ISI 43637 plant parts. Such packaging material includes but is not limited to boxes, plastic bags, etc. The ISI 43637 plant parts may be combined with other plant parts of other plant varieties.

In a further embodiment, the present invention is directed to a method of selecting lettuce plants comprising a) growing ISI 43637 lettuce plants wherein the ISI 43637 plants are grown from lettuce seed having ATCC Accession Number PTA-10858,and b) selecting a plant from step a). In another embodiment, the present invention is further directed to lettuce plants, plant parts and seeds produced by the lettuce plants wherein the lettuce plants are isolated by the selection method of the invention.

In still another embodiment, the present invention is further directed to a method of breeding lettuce plants comprising crossing a lettuce plant with a plant grown from ISI 43637 lettuce seed having ATCC Accession Number PTA-10858. In yet another embodiment, the present invention is further directed to lettuce plants, lettuce parts from the lettuce plants, and seeds produced therefrom where the lettuce plant is isolated by the breeding method of the invention.

IV. DETAILED DESCRIPTION OF THE INVENTION

Origin and Breeding History of the Varieties

ISI 43630

ISI 43630 is a red leaf lettuce variety developed from a hand pollinated cross of the varieties ISI 43030 and ISI 43036 developed by ISI Sementi, Fidenza Italy. The initial cross was made in Fidenza (PR), Italy. The F1 seed harvested was designated as 33-0303026. The cross was made to produce a variety with cherry red color, bubbled leaves, and possible early bolting.

The following year, approximately 30 plants of the F1 seed were planted in Cesena (FC), Italy to increase seed yield. The block was rogued, eliminating self-pollination in plants. The F2 seed was harvested individually.

More than 20 F2 populations were planted in a research and development field trial in Cesena (FC), Italy the following year. Individual F2 plants were selected at market maturity for particular distinguishing characteristics in size, cherry red color, days to bolting, and bubble leaf.

All the following selection stages (from F3 to stability of the variety) underwent trials throughout the growing season, in Cesena (FC), Italy.

A selected line was increased in year 6. Plants that were dark in color, had poor bubbling, and were late bolting, were removed. The plants were harvested individually and the F6 population showed good stability and uniformity.

The F7 seed was uniform without variants, and showed plants with leaves having the desired characteristics. ISI 43630 was evaluated and determined to be uniform and stable in commercial trials and in seed production for a period of two years.

Objective Description of the Variety ISI 43630

Plant Type

ISI 43630 is plant type Cutting/Leaf.

Seed

The seeds are white in color. The seeds do not require light to germinate. The seeds are susceptible to heat dormancy.

Cotyledon to Fourth Leaf Stage

The cotyledons are broad in shape. The shape of the fourth leaf is elongated. The length/width index of the fourth leaf is 16. The apical margin is finely dentate. The basal margin is moderately dentate. The undulation is medium. The green color is light green. The distribution of the anthocyanin is throughout. The concentration is moderate. Rolling is absent. It is uncupped. There is no reflexing.

Mature Leaves

Margin

The incision depth is moderate. The indentation is deeply dentate. The undulations of the apical margin are moderate strong. The green color is light/medium green.

The anthocyanin distribution is throughout and the concentration is moderate. It is medium in size. The glossiness is moderate. Blistering is strong. The leaf is thin. The trichomes are absent.

Plant

The spread of frame leaves is 20 cm. The head diameter is 21 cm. The head shape is non-heading. The head firmness is loose. The butt is slightly concave. The midrib is moderate flattened. The diameter at base of head is 13 mm. The ratio of head diameter/core diameter is 16.1. The core height from base of head to apex is 34 mm.

Bolting

The number of days from first water date to seed stalk emergence was 42 days. The bolting class is medium-medium rapid. The height of mature seed stalk is 65 cm. The spread of bolter plant is 21 cm. The bolter leaves are curved. The margin is dentate. The color is light green. The bolter habit of the terminal inflorescence is present. The bolter habit of the lateral shoots is present. The bolter habit of the basal side shoots is absent.

Maturity

Plants were harvested in the summer. Mature heads were formed in 30 days.

Adaptation

The primary regions of adaptation are Southwest, West Coast, Southeast, and Northeast. The ISI 43630 adapted in the Southwest in the spring, summer, and fall seasons. It did not adapt in the winter. The soil type was both organic and mineral.

Viral Diseases

The ISI 43630 is susceptible to lettuce mosaic, cucumber mosaic, tomato bushy stunt, and lettuce infectious yellows. It is moderately susceptible/moderately resistant to big vein, beet western yellows, and turnip mosaic.

Fungal/Bacterial Diseases

ISI 43630 is susceptible to corky root rot, sclerotinia drop, bacterial leaf spot, bacterial soft rot, anthracnose, and verticillium wilt. It is moderately susceptible/moderately resistant to powdery mildew and botrytis. It is resistant to the CAI-CAVI races of downy mildew.

Insects

ISI 43630 is susceptible to cabbage loopers, root aphids, green peach aphid, lettuce aphid, and pea leafminer.

Physiological Stresses

ISI 43630 is susceptible to brown rib, salt, and cold. It is moderately susceptible/moderately resistant to tipburn, heat, and drought.

Post Harvest Stress

ISI 43630 is susceptible to russet spotting, rusty brown discoloration, internal rib necrosis, brown stain, and pink rib.

Comparisons to ISI 43630

Faradia

The most similar variety used as a comparison to ISI 43630 is Faradia.

Plant Type

Faradia is plant type Cutting/Leaf.

Seed

The seeds are white in color. The seeds do not require light for germination. The seeds are susceptible to heat dormancy.

Cotyledon to Fourth Leaf Stage

The cotyledons are broad in shape. The shape of the fourth leaf is elongated. The length/width index of the fourth leaf is 17.2. The apical margin is coarsely dentate. The basal margin is moderately dentate. The undulation is medium. The green color is medium green. The distribution of the anthocyanin is throughout. The concentration is intense. Rolling is absent. It is uncupped. There is no reflexing.

Mature Leaves

Margin

The incision depth is absent/shallow. The indentation is shallowly dentate. The undulations of the apical margin are moderate. The green color is medium/dark green.

The anthocyanin distribution is throughout and the concentration is intense. It is large in size. Glossiness is moderate. Blistering is moderate. The leaf is thin. The trichomes are absent.

Plant

The spread of frame leaves is 22 cm. The head diameter is 27 cm. The head shape is non-heading. The head firmness is loose. The butt is slightly concave. The midrib is moderately raised. The diameter at base of head is 14 mm. The ratio of head diameter/core diameter is 15. The core height from base of head to apex is 38 mm.

Bolting

The number of days from first water date to seed stalk emergence was 38 days. The bolting class is rapid. The height of mature seed stalk is 75 cm. The spread of bolter plant is 23 cm. The bolter leaves are curved. The margin is dentate. The color is medium green. The bolter habit of the terminal inflorescence is present. The bolter habit of the lateral shoots is present. The bolter habit of the basal side shoots is absent.

Maturity

Plants were harvested in the summer. Mature heads were formed in 26 days.

Viral Diseases

Faradia is susceptible to lettuce mosaic, cucumber mosaic, tomato bushy stunt, beet western yellow, and big vein. It is moderately susceptible/moderately resistant to lettuce infectious yellows, and turnip mosaic.

Fungal/Bacterial Diseases

Faradia is susceptible to corky root rot, bacterial leaf spot, anthracnose, bacterial soft rot, and sclerotinla drop. It is moderately susceptible/moderately resistant to powdery mildew, botrytis, and verticillium wilt. It is resistant to the CAI-CAVI races of downy mildew.
Insects
Faradia is susceptible to cabbage loopers and pea leafminer. It is moderately resistant/moderately susceptible to root aphids and green peach aphid. It is also resistant to lettuce aphid.
Physiological Stresses
Faradia is susceptible to brown rib and salt. It is moderately susceptible/moderately resistant to tipburn, heat, drought, and cold.
Post Harvest Stress
Faradia is susceptible to russet spotting, rusty brown discoloration, internal rib necrosis, brown stain, and pink rib.

Redlo

The standard regional control variety used is Redlo.
Plant Type
Redlo is plant type Cutting/Leaf.
Seed
The seeds are white in color. The seeds do not require light for germination. The seeds are susceptible to heat dormancy.
Cotyledon to Fourth Leaf Stage
The cotyledons are broad in shape. The shape of the fourth leaf is elongated. The length/width index of the fourth leaf is 1.71. The apical margin is moderately dentate. The basal margin is coarsely dentate. The undulation is medium. The green color is medium. The distribution of the anthocyanin is throughout. The concentration is intense. Rolling is absent. It is uncupped. There is no reflexing.
Mature Leaves
Margin
The incision depth is shallow. The indentation is shallowly dentate. The undulations of the apical margin is moderate. The green color is medium/dark green.
The anthocyanin distribution is throughout and the concentration is intense. It is medium in size. Glossiness is moderate. Blistering is strong. The leaf is thin. The trichomes are absent.
Plant
The spread of frame leaves is 19 cm. The head diameter is 23 cm. The head shape is non-heading. The head firmness is loose. The butt is flat. The midrib is moderately raised. The diameter at base of head is 14 mm. The ratio of head diameter/core diameter is 16.4. The core height from base of head to apex is 39 mm.
Bolting
The number of days from first water date to seed stalk emergence was 37 days. The bolting class is rapid. The height of mature seed stalk is 75 cm. The spread of bolter plant is 24 cm. The bolter leaves are curved. The margin is dentate. The color is medium green. The bolter habit of the terminal inflorescence is present. The bolter habit of the lateral shoots is present. The bolter habit of the basal side shoots is absent.
Maturity
Plants were harvested in the summer. Mature heads were formed in 28 days.
Viral Diseases
Redlo is susceptible to lettuce mosaic, cucumber mosaic, tomato bushy stunt, turnip mosaic, and big vein. It is moderately susceptible/moderately resistant to lettuce infectious yellows and beet western yellows.
Fungal/Bacterial Diseases
Redlo is susceptible to corky root rot, bacterial leaf spot, anthracnose, bacterial soft rot, verticillium wilt, and sclerotinla drop. It is moderately susceptible/moderately resistant to powdery mildew, and botrytis. It is resistant to the CAI-CAVI races of downy mildew.
Insects
Redlo is susceptible to cabbage loopers, root aphids, green peach aphid, lettuce aphid, and pea leafminer.
Physiological Stresses
Redlo is susceptible to brown rib and cold. It is moderately susceptible/moderately resistant to tipburn, heat, drought, and salt.
Post Harvest Stress
Redlo is susceptible to russet spotting, rusty brown discoloration, internal rib necrosis, brown stain, and pink rib.

ISI 43637

ISI 43637 is a red leaf lettuce variety developed from a hand pollinated cross of the varieties ISI 43030 and ISI 43037 developed by ISI Sementi, Fidenza Italy. The initial cross was made in Fidenza (PR), Italy. The F1 seed harvested was designated as 33-0304036. The cross was made to produce a variety with dark red color, bubbled leaves, and possible early bolting.
The following year, approximately 35 plants of the F1 seed were planted in Cesena (FC), Italy to increase seed yield. The block was rogued, eliminating self-pollination in plants. The F2 seed was harvested individually.
More than 25 F2 populations were planted in a research and development field trial in Cesena (FC), Italy the following year. Individual F2 plants were selected at market maturity for particular distinguishing characteristics in bubble leaf with dark red color, and days to bolting.
All the following selection stage (from F3 to stability of the variety) underwent trials throughout the growing season, in Cesena (FC), Italy.
A selected line was increased in year 5. Plants that had cherry colored leaves, poor bubbling, and were late bolting, were removed. The plants were harvested individually and the F5 population showed good stability and uniformity.
The F6 seed was uniform without variants, and showed plants with leaves having the desired characteristics. ISI 43637 was evaluated and determined to be uniform and stable in commercial trials, and seed production for a period of two years.

Objective Description of the Variety ISI 43637

Plant type
ISI 43637 is plant type Cutting/Leaf.
Seed
The seeds are white in color. The seeds do not require light for germination. The seeds are susceptible to heat dormancy.
Cotyledon to Fourth Leaf Stage
The cotyledons are broad in shape. The shape of the fourth leaf is elongated. The length/width index of the fourth leaf is 16.2. The apical margin is finely dentate. The basal margin is moderately dentate. The undulation is medium. The green color is light green. The distribution of the anthocyanin is throughout. The concentration is intense. Rolling is absent. It is uncupped. There is no reflexing.
Mature Leaves
Margin
The incision depth is moderate/shallow. The indentation is deeply dentate. The undulations of the apical margin are moderate strong. The green color is medium green.
The anthocyanin distribution is throughout and the concentration is intense. It is medium in size. The glossiness is moderate. Blistering is strong. The leaf is thin. The trichomes are absent.

Plant

The spread of frame leaves is 21 cm. The head diameter is 23 cm. The head shape is non-heading. The head firmness is loose. The butt is slightly concave. The midrib is moderate flattened. The diameter at base of head is 14 mm. The ratio of head diameter/core diameter is 16.4. The core height from base of head to apex is 34 mm.

Bolting

The number of days from first water date to seed stalk emergence was 40 days. The bolting class is medium-medium rapid. The height of mature seed stalk is 67 cm. The spread of bolter plant is 23 cm. The bolter leaves are curved. The margin is dentate. The color is light medium green. The bolter habit of the terminal inflorescence is present. The bolter habit of the lateral shoots is present. The bolter habit of the basal side shoots is absent.

Maturity

Plants were harvested in the summer. Mature heads were formed in 28 days.

Adaptation

The primary regions of adaptation are Southwest, North Central, West Coast, Southeast, and Northeast. The ISI 43637 adapted in the Southwest in the spring, summer, and fall seasons. It did not adapt in the winter. The soil type was both organic and mineral.

Viral Diseases

ISI 43637 is susceptible to lettuce mosaic, cucumber mosaic, tomato bushy stunt, and lettuce infectious yellows. It is moderately susceptible/moderately resistant to big vein, beet western yellows, and turnip mosaic.

Fungal/Bacterial Diseases

ISI 43637 is susceptible to corky root rot, sclerotinia drop, bacterial leaf spot, bacterial soft rot, anthracnose, and verticillium wilt. It is moderately susceptible/moderately resistant to powdery mildew and botrytis. It is resistant to the CAI-CAVI races of downy mildew.

Insects

ISI 43637 is susceptible to cabbage loopers, root aphids, green peach aphid, lettuce aphid, and pea leafminer.

Physiological Stresses

ISI 43637 is susceptible to brown rib, salt, and cold. It is moderately susceptible/moderately resistant to tipburn, heat, and drought.

Post Harvest Stress

ISI 43637 is susceptible to russet spotting, rusty brown discoloration, internal rib necrosis, brown stain, and pink rib.

Comparisons to ISI 43637

Faradia

The most similar variety used as a comparison to ISI 43637 is Faradia. Plant type Faradia is plant type Cutting/Leaf.

Seed

The seeds are white in color. The seeds do not require light for germination. The seeds are susceptible to heat dormancy.

Cotyledon to Fourth Leaf Stage

The cotyledons are broad in shape. The shape of the fourth leaf is elongated. The length/width index of the fourth leaf is 17.2. The apical margin is coarsely dentate. The basal margin is moderately dentate. The undulation is medium. The green color is medium green. The distribution of the anthocyanin is throughout. The concentration is intense. Rolling is absent. It is uncupped. There is no reflexing.

Mature Leaves

Margin

The incision depth is absent/shallow. The indentation is shallowly dentate. The undulations of the apical margin are moderate. The green color is medium/dark green.

The anthocyanin distribution is throughout and the concentration is intense. It is large in size. Glossiness is moderate. Blistering is moderate. The leaf is thin. The trichomes are absent.

Plant

The spread of frame leaves is 22 cm. The head diameter is 27 cm. The head shape is non-heading. The head firmness is loose. The butt is slightly concave. The midrib is moderately raised. The diameter at base of head is 14 mm. The ratio of head diameter/core diameter is 15. The core height from base of head to apex is 38 mm.

Bolting

The number of days from first water date to seed stalk emergence was 38 days. The bolting class is rapid. The height of mature seed stalk is 75 cm. The spread of bolter plant is 23 cm. The bolter leaves are curved. The margin is dentate. The color is medium green. The bolter habit of the terminal inflorescence is present. The bolter habit of the lateral shoots is present. The bolter habit of the basal side shoots is absent.

Maturity

Plants were harvested in the summer. Mature heads were formed in 26 days.

Viral Diseases

Faradia is susceptible to lettuce mosaic, cucumber mosaic, tomato bushy stunt, beet western yellow, and big vein. It is moderately susceptible/moderately resistant to lettuce infectious yellows and turnip mosaic.

Fungal/Bacterial Diseases

Faradia is susceptible to corky root rot, bacterial leaf spot, anthracnose, bacterial soft rot, and sclerotinla drop. It is moderately susceptible/moderately resistant to powdery mildew, botrytis, and verticillium wilt. It is resistant to the CAI-CAVI races of downy mildew.

Insects

Faradia is susceptible to cabbage loopers and pea leafminer. It is moderately resistant/moderately susceptible to root aphids and green peach aphid. It is also resistant to lettuce aphid.

Physiological Stresses

Faradia is susceptible to brown rib and salt. It is moderately susceptible/moderately resistant to tipburn, heat, drought, and cold.

Post Harvest Stress

Faradia is susceptible to russet spotting, rusty brown discoloration, internal rib necrosis, brown stain, and pink rib.

Redlo

The standard regional check variety used is Redlo.

Plant type

Redlo is plant type Cutting/Leaf.

Seed

The seeds are white in color. The seeds do not require light for germination. The seeds are susceptible to heat dormancy.

Cotyledon to Fourth Leaf Stage

The cotyledons are broad in shape. The shape of the fourth leaf is elongated. The length/width index of the fourth leaf is 1.71. The apical margin is moderately dentate. The basal margin is coarsely dentate. The undulation is medium. The green color is medium. The distribution of the anthocyanin is throughout. The concentration is intense. Rolling is absent. It is uncupped. There is no reflexing.

Mature Leaves
Margin

The incision depth is shallow. The indentation is shallowly dentate. The undulations of the apical margin is moderate. The green color is medium/dark green.

The anthocyanin distribution is throughout and the concentration is intense. It is medium in size. Glossiness is moderate. Blistering is strong. The leaf is thin. The trichomes are absent.
Plant The spread of frame leaves is 19 cm. The head diameter is 23 cm. The head shape is non-heading. The head firmness is loose. The butt is flat. The midrib is moderately raised. The diameter at base of head is 14 mm. The ratio of head diameter/core diameter is 16.4. The core height from base of head to apex is 39 mm.
Bolting The number of days from first water date to seed stalk emergence was 37 days. The bolting class is rapid. The height of mature seed stalk is 75 cm. The spread of bolter plant is 24 cm. The bolter leaves are curved. The margin is dentate. The color is medium green. The bolter habit of the terminal inflorescence is present. The bolter habit of the lateral shoots is present. The bolter habit of the basal side shoots is absent.
Maturity Plants were harvested in the summer. Mature heads were formed in 28 days.
Viral Diseases Redlo is susceptible to lettuce mosaic, cucumber mosaic, tomato bushy stunt, turnip mosaic, and big vein. It is moderately susceptible/moderately resistant to lettuce infectious yellows and beet western yellows.
Fungal/Bacterial Diseases Redlo is susceptible to corky root rot, bacterial leaf spot, anthracnose, bacterial soft rot, verticillium wilt and sclerotinla drop. It is moderately susceptible/moderately resistant to powdery mildew, and botrytis. It is resistant to the CAI-CAVI races of downy mildew.
Insects Redlo is susceptible to cabbage loopers, root aphids, green peach aphid, lettuce aphid, and pea leafminer.
Physiological Stresses Redlo is susceptible to brown rib and cold. It is moderately susceptible/moderately resistant to tipburn, heat, drought, and salt.
Post Harvest Stress Redlo is susceptible to russet spotting, rusty brown discoloration, internal rib necrosis, and brown stain, and pink rib.

Deposit Information

Applicants have made available to the public without restriction a deposit of at least 2500 seeds of lettuce variety ISI 43630 with the American Type Culture Collection (ATCC), P.O. Box 1549, MANASSAS, Va. 20108 USA, with a deposit on Apr. 26,2010, which has been assigned ATCC number PTA-10859.

The deposit will be maintained in the ATCC depository, which is a public depository, for a period of 30 years, or 5 years after the most recent request, or for the effective life of the patent, whichever is longer, and will be replaced if the deposit becomes nonviable during that period.

Applicants have made available to the public without restriction a deposit of at least 2500 seeds of lettuce variety ISI 43637 with the American Type Culture Collection (ATCC), P.O. Box 1549, MANASSAS, Va. 20108 USA, with a deposit on Apr. 26,2010 which has been assigned ATCC number PTA-10858.

The deposit will be maintained in the ATCC depository, which is a public depository, for a period of 30 years, or 5 years after the most recent request, or for the effective life of the patent, whichever is longer, and will be replaced if the deposit becomes nonviable during that period.

The invention claimed is:

1. Lettuce seed designated as ISI 43630 having ATCC Accession Number PTA-10859.

2. A lettuce plant produced by growing the seed of claim 1.

3. A plant part from the plant of claim 2.

4. The plant part of claim 3 wherein said part is a head.

5. The plant part of claim 3 wherein said part is a leaf or a portion thereof.

6. A lettuce plant having all the physiological and morphological characteristics of the lettuce plant of claim 2.

7. A plant part from the plant of claim 6.

8. The plant part of claim 7 wherein said part is a head.

9. The plant part of claim 7 wherein said part is a leaf or a portion thereof.

10. Pollen of the plant of claim 2.

11. An ovule of the plant of claim 2.

12. A tissue culture of the plant of claim 2.

13. A method of making lettuce seeds comprised of crossing the plant of claim 2 with another lettuce plant and harvesting seed therefrom.

14. An $F_1$ hybrid lettuce plant having ISI 43630 as a parent where ISI 43630 is grown from the seed of claim 1.

15. A method of making lettuce variety ISI 43630, said method comprising selecting seeds from the cross of one ISI 43630 plant with another ISI 43630 plant, a sample of ISI 43630 lettuce seed having been deposited under ATCC Accession Number PTA-10859.

16. Lettuce seed designated as ISI 43637 having ATCC Accession Number PTA-10858.

17. A lettuce plant produced by growing the seed of claim 16.

18. A plant part from the plant of claim 17.

19. The plant part of claim 18 wherein said part is a head.

20. The plant part of claim 18 wherein said part is a leaf or a portion thereof.

21. A lettuce plant having all the physiological and morphological characteristics of the lettuce plant of claim 17.

22. A plant part from the plant of claim 21.

23. The plant part of claim 22 wherein said part is a head.

24. The plant part of claim 22 wherein said part is a leaf or a portion thereof.

25. Pollen of the plant of claim 17.

26. An ovule of the plant of claim 17.

27. A tissue culture of the plant of claim 17.

28. A method of making lettuce seeds comprised of crossing the plant of claim 17 with another lettuce plant and harvesting seed therefrom.

29. An $F_1$ hybrid lettuce plant having ISI 43637 as a parent where ISI 43637 is grown from the seed of claim 16.

30. A method of making lettuce variety ISI 43637, said method comprising selecting seeds from the cross of one ISI 43637 plant with another ISI 43637 plant, a sample of ISI 43637 lettuce seed having been deposited under ATCC Accession Number PTA-10858.

* * * * *